(12) United States Patent
Tanno et al.

(10) Patent No.: US 12,183,000 B2
(45) Date of Patent: Dec. 31, 2024

(54) ESTIMATING DEVICE, ESTIMATING METHOD, AND ESTIMATING PROGRAM

(71) Applicant: NTT Communications Corporation, Tokyo (JP)

(72) Inventors: Ryosuke Tanno, Chofu (JP); Syuhei Asano, Funabashi (JP)

(73) Assignee: NTT COMMUNICATIONS CORPORATION, Tokyo (JP)

( * ) Notice: Subject to any disclaimer, the term of this patent is extended or adjusted under 35 U.S.C. 154(b) by 441 days.

(21) Appl. No.: 17/709,408

(22) Filed: Mar. 31, 2022

(65) Prior Publication Data
US 2022/0222821 A1 Jul. 14, 2022

Related U.S. Application Data

(63) Continuation of application No. PCT/JP2020/037553, filed on Oct. 2, 2020.

(30) Foreign Application Priority Data

Oct. 4, 2019 (JP) .................................. 2019-183965

(51) Int. Cl.
*G06T 7/00* (2017.01)
*G06T 7/73* (2017.01)
(Continued)

(52) U.S. Cl.
CPC .............. *G06T 7/0012* (2013.01); *G06T 7/73* (2017.01); *G06V 10/761* (2022.01);
(Continued)

(58) Field of Classification Search
CPC .... G06V 40/103; G06V 10/82; G06V 10/764; G06V 40/10; G06V 40/23; G06V 20/59; G06V 20/593; G06V 10/34; G06V 10/80; G06V 20/647; G06V 20/20; G06V 20/52; G06V 20/56; G06V 20/58; G06V 40/107; G06V 40/171; G06V 40/173; G06V 40/28;
(Continued)

(56) References Cited

U.S. PATENT DOCUMENTS

2020/0272888 A1* 8/2020 Wang .................... G06V 40/103
2020/0311400 A1* 10/2020 Wakayama ............ G06V 40/10

FOREIGN PATENT DOCUMENTS

CN 101882326 A 11/2010
CN 103155003 A 6/2013
(Continued)

OTHER PUBLICATIONS

Office Action issued Oct. 25, 2024 in Chinese Patent Application No. 202080058178.5, 14 pages.

*Primary Examiner* — Ajibola A Akinyemi
(74) *Attorney, Agent, or Firm* — XSENSUS LLP (57) ABSTRACT

An estimating device includes processing circuitry configured to acquire image data lacking part of a body of a person, restore a defective part of the body of the person in the image data by using the image data acquired as an input, and using a whole body restoration model for restoring the defective part of the body of the person in the image data, and estimate skeleton data by using the image data restored as an input, and using a skeleton estimation model for estimating the skeleton data related to a skeleton of the person.

4 Claims, 6 Drawing Sheets

(51) Int. Cl.
*G06V 10/74* (2022.01)
*G06V 10/77* (2022.01)
*G06V 40/10* (2022.01)

(52) U.S. Cl.
CPC ........ *G06V 10/7715* (2022.01); *G06V 40/103* (2022.01); *G06V 2201/033* (2022.01); *G06V 2201/07* (2022.01)

(58) Field of Classification Search
CPC ...... G06V 40/50; G06V 10/242; G06V 10/26; G06V 10/44; G06V 10/454; G06V 10/462
USPC ........................................................ 382/128
See application file for complete search history.

(56) References Cited

FOREIGN PATENT DOCUMENTS

| | | |
|---|---|---|
| CN | 105653887 A | 6/2016 |
| CN | 108319930 A | 7/2018 |
| JP | 2015-28702 A | 2/2015 |
| JP | 2018-13999 A | 1/2018 |
| TW | 201933276 A | 8/2019 |
| WO | 2016/159165 A1 | 10/2016 |

\* cited by examiner

ESTIMATING DEVICE, ESTIMATING METHOD, AND ESTIMATING PROGRAM

CROSS-REFERENCE TO RELATED APPLICATION

This application is a continuation application of International Application No. PCT/JP2020/037553, filed on Oct. 2, 2020 which claims the benefit of priority of the prior Japanese Patent Application No. 2019-183965, filed on Oct. 4, 2019, the entire contents of which are incorporated herein by reference.

FIELD

The present invention relates to an estimating device, an estimating method, and an estimating program.

BACKGROUND

There is known a technique of performing personal authentication by using various kinds of biometric authentication. As such an authentication technique, for example, there is known a technique of performing skeleton estimation for estimating position coordinates of a skeleton from image data including the whole body of a person as an authentication target, and performing personal authentication based on an estimation result. The related technologies are described, for example, in: Japanese Laid-open Patent Publication No. 2018-013999.

However, a related method of skeleton estimation has the problem that skeleton estimation cannot be performed with high accuracy in some cases. For example, the related method of skeleton estimation has the problem that accuracy of skeleton estimation is lowered in a case in which an image includes only part of a body of a person as an authentication target in image data.

SUMMARY

It is an object of the present invention to at least partially solve the problems in the related technology.

According to an aspect of the embodiments, an estimating device includes: processing circuitry configured to: acquire image data lacking part of a body of a person; restore a defective part of the body of the person in the image data by using the image data acquired as an input, and using a whole body restoration model for restoring the defective part of the body of the person in the image data; and estimate skeleton data by using the image data restored as an input, and using a skeleton estimation model for estimating the skeleton data related to a skeleton of the person.

The above and other objects, features, advantages and technical and industrial significance of this invention will be better understood by reading the following detailed description of presently preferred embodiments of the invention, when considered in connection with the accompanying drawings.

DESCRIPTION OF EMBODIMENTS

The following describes embodiments of an estimating device, an estimating method, and an estimating program according to the present application in detail based on the drawings. The estimating device, the estimating method, and the estimating program according to the present application are not limited to the embodiments.

First Embodiment

The following embodiment describes a configuration of an estimating device 10 according to a first embodiment and a procedure of processing performed by the estimating device 10 in order, and lastly describes an effect of the first embodiment.

Configuration of Estimating Device

Figure 1:
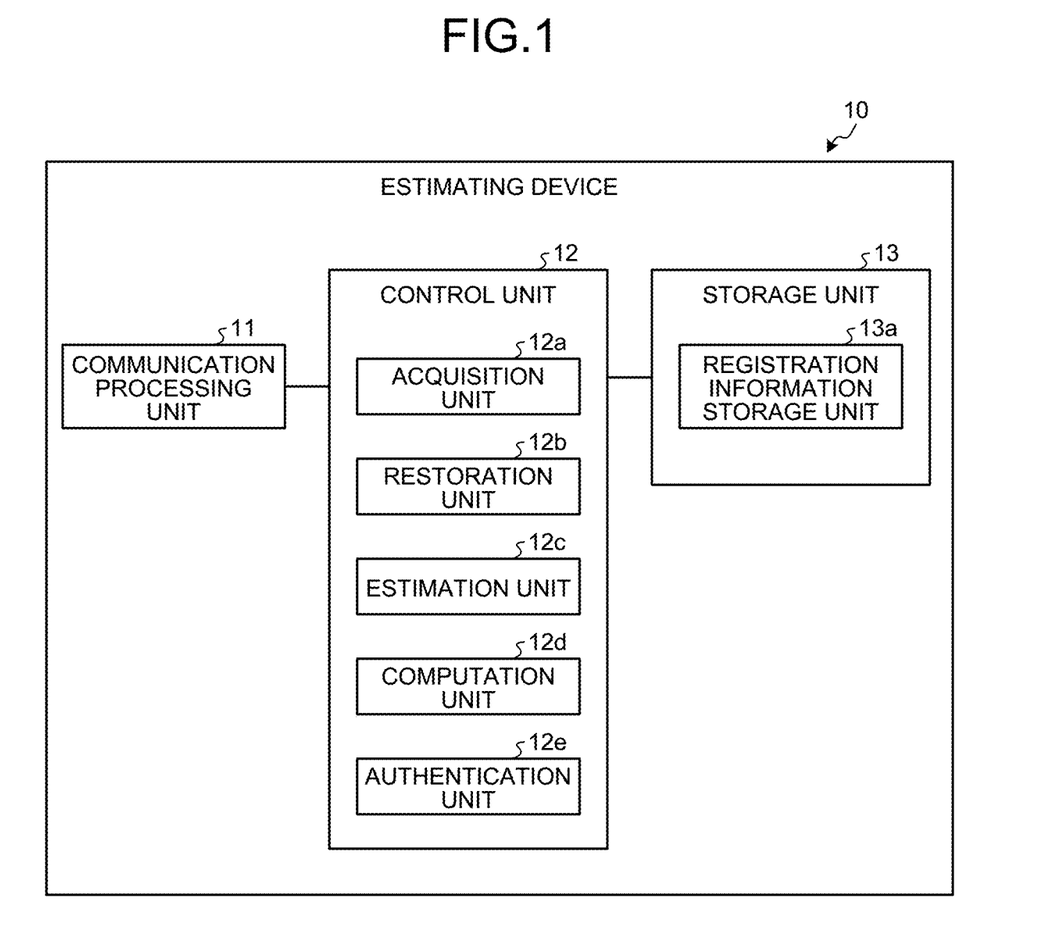
FIG. 1 is a block diagram illustrating a configuration example of an estimating device according to a first embodiment.

First, the following describes the configuration of the estimating device 10 with reference to FIG. 1. FIG. 1 is a block diagram illustrating a configuration example of the estimating device according to the first embodiment. The estimating device 10 acquires image data reflecting part of a body of a person as an authentication target to perform personal authentication, and restores a defective part of the person as the authentication target from the acquired image data to estimate skeleton data of the person. The estimating device 10 is a device for performing personal authentication by calculating a similarity between the estimated skeleton data and skeleton data as a correct answer.

As illustrated in FIG. 1, the estimating device 10 includes a communication processing unit 11, a control unit 12, and a storage unit 13. The following describes processing performed by each unit included in the estimating device 10.

The communication processing unit 11 controls communication related to various kinds of information exchanged with a connected device. For example, the communication processing unit 11 receives, from an external device, image data as a processing target of skeleton estimation. The storage unit 13 stores data and computer programs used for various kinds of processing performed by the control unit 12 and includes a registration information storage unit 13a. For example, the storage unit 13 is a storage device such as a semiconductor memory element including a random access memory (RAM), a flash memory, and the like.

The registration information storage unit 13a stores skeleton data registered in advance by a user. For example, the registration information storage unit 13a stores, as the skeleton data, skeleton data that is estimated from an image of the whole body of the user in a state in which the user makes a predetermined pose (for example, raising both hands) in front of a camera. This pose may be freely determined by the user at the time of registration, or may be a pose that is determined in advance and notified to only an authorized user.

The control unit 12 includes an internal memory for storing requested data and computer programs specifying various processing procedures and executes various kinds of processing therewith. For example, the control unit 12 includes an acquisition unit 12a, a restoration unit 12b, an estimation unit 12c, a computation unit 12d, and an authentication unit 12e. Herein, the control unit 12 is, for example, an electronic circuit such as a central processing unit (CPU), a micro processing unit (MPU), and a graphical processing unit (GPU), or an integrated circuit such as an application specific integrated circuit (ASIC) and a field programmable gate array (FPGA).

Figure 2:
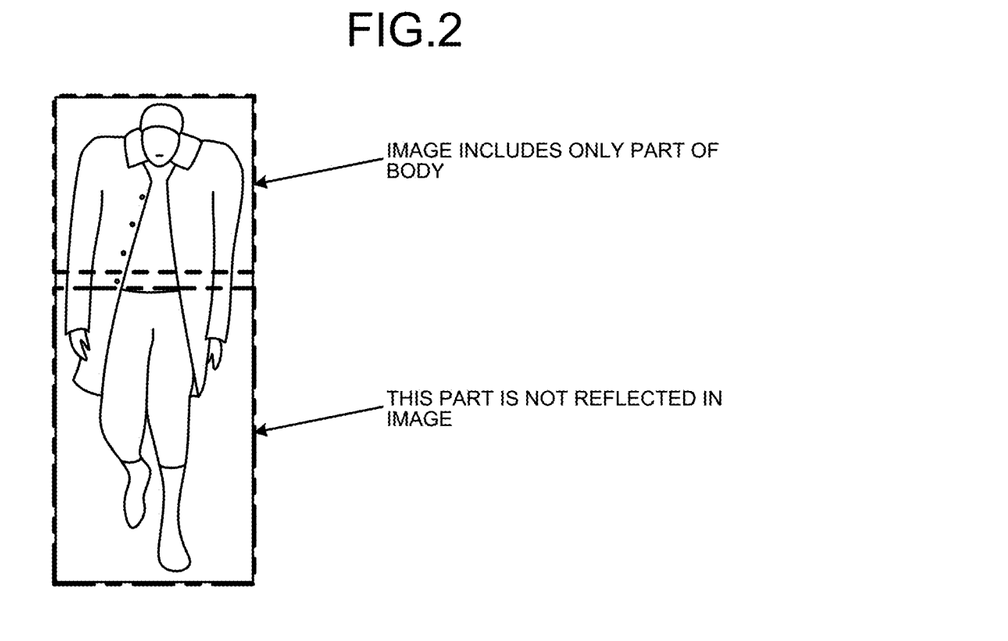
FIG. 2 is a diagram for explaining image data lacking part of a body of a person.
Figure 3:
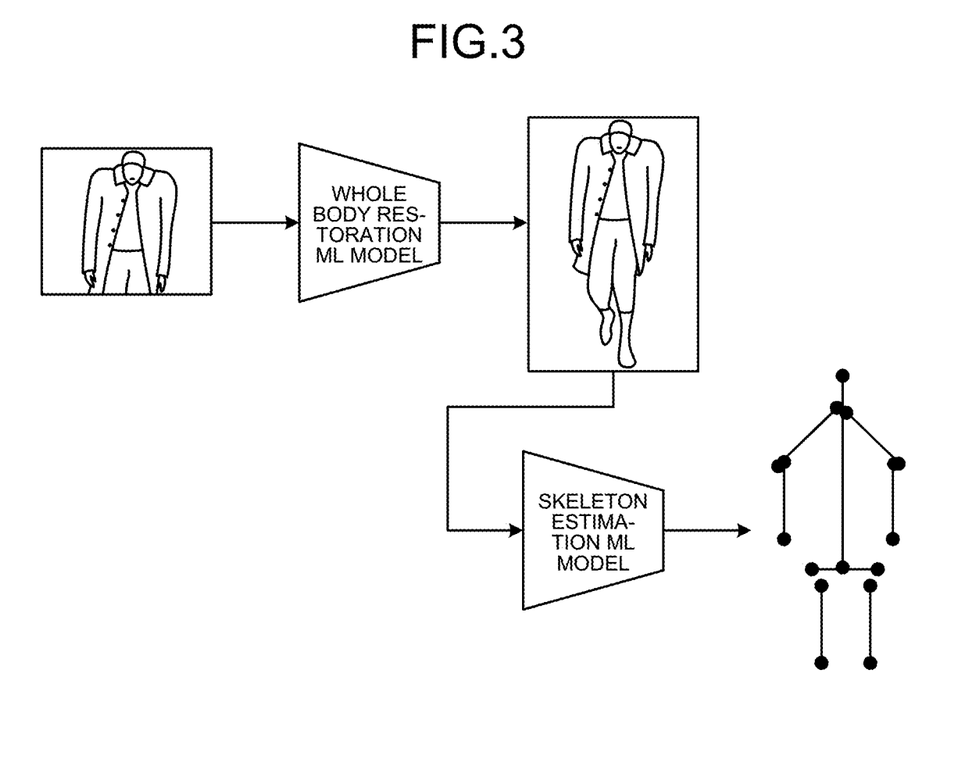
FIG. 3 is a diagram for explaining an outline of skeleton estimation processing performed by the estimating device according to the first embodiment.

The acquisition unit 12a acquires image data lacking part of the body of the person. For example, the acquisition unit 12a acquires the image data from a camera by which the person as the authentication target is photographed, and outputs the image data to the restoration unit 12b. The image data acquired herein is assumed to be an image including only part of the body of the person as exemplified in FIG. 2. In the image data in the example of FIG. 2, it is assumed that the image includes only an upper half of the body above a waist, and a lower half of the body below the waist is not reflected in the image.

The restoration unit 12b uses the image data acquired by the acquisition unit 12a as an input, and restores a defective part of the body of the person in the image data by using a whole body restoration model for restoring the defective part of the body of the person in the image data. That is, the restoration unit 12b inputs the image data lacking part of the body of the person to the whole body restoration model, and acquires the image data output from the whole body restoration model, the image data in which the defective part is restored. This whole body restoration model is a pre-learned model generated in advance.

The estimation unit 12c uses the image data restored by the restoration unit 12b as an input, and estimates the skeleton data by using a skeleton estimation model for estimating the skeleton data related to a skeleton of the person. This skeleton estimation model is a pre-learned model that is learned by using image data including the whole body, and is a model that is generated assuming that image data including the whole body or most part of the body is input as input data.

For example, the estimation unit 12c specifies positions of respective parts of the skeleton of the person in the image data by inputting the image data to the skeleton estimation model, and estimates positions of a "right shoulder", a "right upper arm", a "right forearm", a "left shoulder", a "left upper arm", a "left forearm", a "right thigh", a "right crus", a "left thigh", and a "left crus" as portions corresponding to respective articulations.

Figure 4:
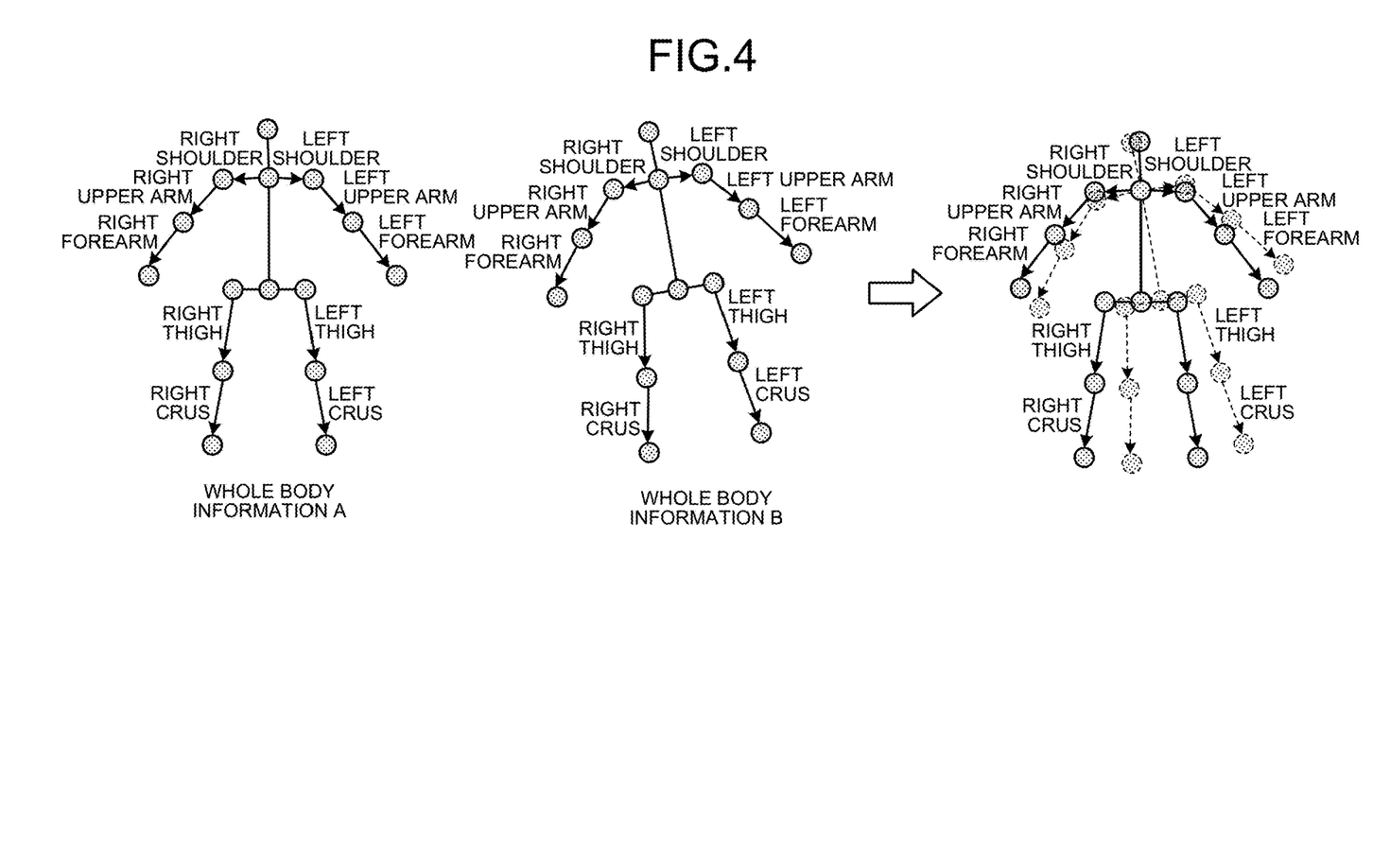
FIG. 4 is a diagram for explaining a processing example for calculating a similarity of a skeleton.

The computation unit 12d computes a similarity between the skeleton data estimated by the estimation unit 12c and the skeleton data registered in advance. The following describes a processing example for calculating the similarity of the skeleton with reference to FIG. 4. FIG. 4 is a diagram for explaining a processing example for computing the similarity of the skeleton.

As exemplified in FIG. 4, the computation unit 12d specifies positions of respective parts of the skeleton for each of whole body information A as the skeleton data estimated by the estimation unit 12c and whole body information B as the skeleton data stored in advance, and specifies angles of the "right shoulder", the "right upper arm", the "right forearm", the "left shoulder", the "left upper arm", the "left forearm", the "right thigh", the "right crus", the "left thigh", and the "left crus" as respective articulations. The skeleton data is represented by points indicating the respective parts, and lines or arrows connecting adjacent points. For example, the computation unit 12d computes closeness between angles of vectors as a similarity using a cosine similarity for the respective articulations. In this case, a value becomes closer to 1 as angles of two vectors become closer to each other. For example, the computation unit 12d may obtain the similarity for each of all the articulations, and compute a total value of similarities of the respective articulations as the similarity of the skeleton of the user.

The authentication unit 12e determines whether the similarity computed by the computation unit 12d is equal to or larger than a predetermined threshold. If the similarity is equal to or larger than the predetermined threshold, the authentication unit 12e determines that authentication has succeeded, and if the similarity is smaller than the predetermined threshold, the authentication unit 12e determines that authentication has failed. The estimating device 10 may perform processing up to estimation processing for the skeleton data, and similarity computation processing and authentication processing may be performed by another device.

Processing Procedure of Estimating Device

Figure 5:
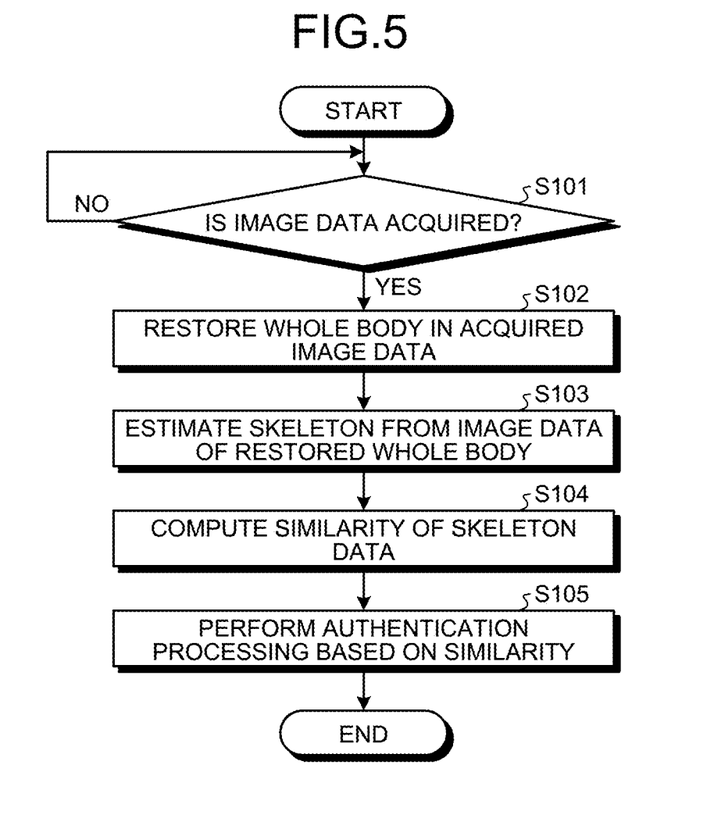
FIG. 5 is a flowchart illustrating an example of a procedure of processing performed by the estimating device according to the first embodiment.

Next, the following describes an example of a processing procedure performed by the estimating device 10 according to the first embodiment with reference to FIG. 5. FIG. 5 is a flowchart illustrating an example of a procedure of processing performed by the estimating device according to the first embodiment.

As exemplified in FIG. 5, in the estimating device 10, if the acquisition unit 12a acquires the image data lacking part of the body of the person (Yes at Step S101), the restoration unit 12b restores the defective part of the body of the person in the image data acquired by the acquisition unit 12a (Step S102). Specifically, the restoration unit 12b uses the image data acquired by the acquisition unit 12a as an input, and restores the defective part of the body of the person in the image data by using the whole body restoration model for restoring the defective part of the body of the person in the image data.

The estimation unit 12c then estimates the skeleton from the image data of the whole body in which the defective part is restored (Step S103). Specifically, the estimation unit 12c uses the image data restored by the restoration unit 12b as an input, and estimates the skeleton data by using the skeleton estimation model for estimating the skeleton data related to the skeleton of the person.

Subsequently, the computation unit 12d computes the similarity between the skeleton data estimated by the estimation unit 12c and the skeleton data registered in advance (Step S104). The authentication unit 12e then determines whether the similarity computed by the computation unit 12d is equal to or larger than the predetermined threshold. If the similarity is equal to or larger than the predetermined threshold, the authentication unit 12e determines that authentication has succeeded, and if the similarity is smaller than the predetermined threshold, the authentication unit 12e determines that authentication has failed (Step S105).

Effect of First Embodiment

The estimating device 10 according to the first embodiment acquires the image data lacking part of the body of the person, uses the acquired image data as an input, and restores the defective part of the body of the person in the image data by using the whole body restoration model for restoring the defective part of the body of the person in the image data. The estimating device 10 then uses the restored image data as an input, and estimates the skeleton data by using the skeleton estimation model for estimating the skeleton data related to the skeleton of the person. Thus, the estimating device 10 can maintain accuracy of skeleton estimation, and can maintain accuracy of authentication processing even with the image data including only part of the body of the person.

In addition, the estimating device 10 requests image data of the whole body for learning of the skeleton estimation model, and image data reflecting only part of the body is not requested to be prepared for learning, so that learning of the skeleton estimation model can be easily performed.

Modification

The estimating device may determine whether the image data includes minimum portions requested for authentication at the time of restoring the defective part of the body of the person in the image data lacking part of the body of the person, and does not necessarily perform the authentication processing if the image data does not include the minimum portions requested for authentication. Herein, it is assumed that the minimum portions requested for authentication can be set in advance. For example, in a case of performing authentication by determining whether the user is making a pose of raising both hands, it is determined whether the image data includes an upper half of the body of the user as the minimum portions requested for authentication.

Figure 6:
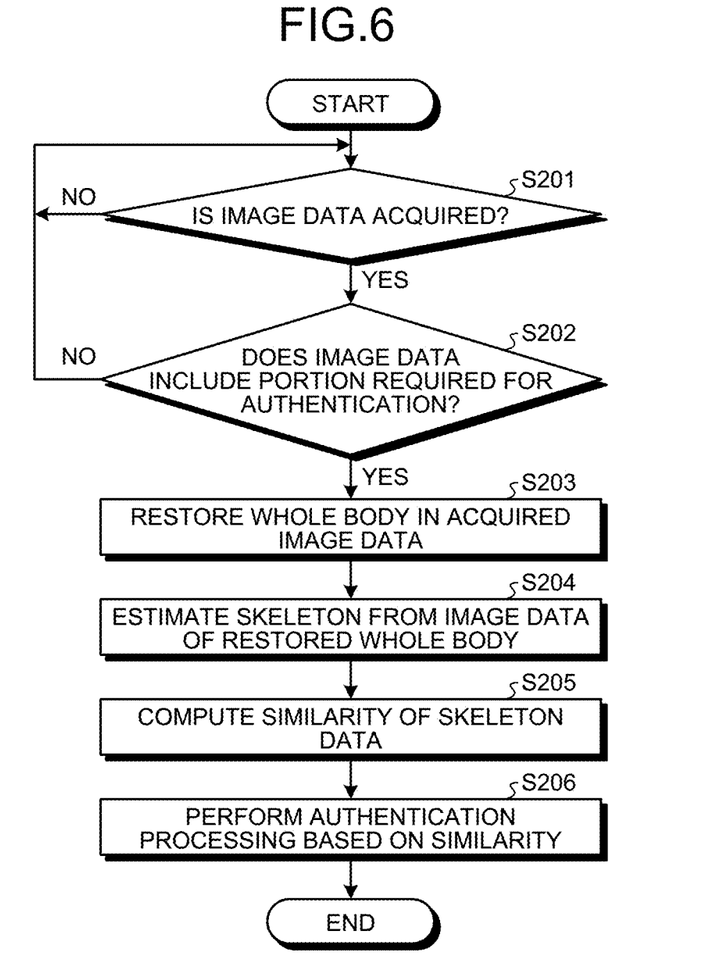
FIG. 6 is a flowchart illustrating an example of a procedure of processing performed by an estimating device according to a modification.

As a modification, the following describes processing in a case of determining whether the image data includes the minimum portions requested for authentication as described above with reference to FIG. 6. FIG. 6 is a flowchart illustrating an example of a procedure of the processing performed by the estimating device according to the modification.

As exemplified in FIG. 6, in the estimating device according to the modification, if the acquisition unit 12*a* acquires the image data lacking part of the body of the person (Yes at Step S201), the acquisition unit 12*a* determines whether the image data includes a portion requested for authentication (Step S202). For example, the acquisition unit 12*a* analyzes the acquired image data, specifies a part of the body included in the image data, and determines whether the image data includes a portion of the body requested for authentication.

As a result, if it is determined that the image data does not include the portion requested for authentication (No at Step S202), the process returns to Step S201, and the acquisition unit 12*a* acquires the image again. If the acquisition unit 12*a* determines that the image data includes the portion requested for authentication (Yes at Step S202), the restoration unit 12*b* restores the defective part of the body of the person in the image data acquired by the acquisition unit 12*a* (Step S203).

The estimation unit 12*c* then estimates the skeleton from the image data of the whole body in which the defective part is restored (Step S204). Subsequently, the computation unit 12*d* computes the similarity between the skeleton data estimated by the estimation unit 12*c* and the skeleton data registered in advance (Step S205). The authentication unit 12*e* then determines whether the similarity computed by the computation unit 12*d* is equal to or larger than the predetermined threshold. If the similarity is equal to or larger than the predetermined threshold, the authentication unit 12*e* determines that authentication has succeeded, and if the similarity is smaller than the predetermined threshold, the authentication unit 12*e* determines that authentication has failed (Step S206).

In this way, the estimating device according to the modification performs restoration processing for the whole body or authentication processing after determining whether the image data includes the minimum portions requested for authentication, so that the restoration processing for the whole body is prevented from being performed in a state in which a part of the body important for performing the authentication processing is not reflected in the image, and erroneous authentication processing is prevented from being performed. Accordingly, accuracy of the authentication processing can be maintained.

System Configuration and Like

The components of the devices illustrated in the drawings are merely conceptual, and it is not requested that they are physically configured as illustrated necessarily. That is, specific forms of distribution and integration of the devices are not limited to those illustrated in the drawings. All or part thereof may be functionally or physically distributed/integrated in arbitrary units depending on various loads or usage states. All or optional part of the processing functions performed by the respective devices may be implemented by a CPU or a GPU and computer programs analyzed and executed by the CPU or the GPU, or may be implemented as hardware using wired logic.

Among pieces of the processing described in the present embodiment, all or part of the pieces of processing described to be automatically performed can be manually performed, or all or part of the pieces of processing described to be manually performed can be automatically performed by using a known method. Additionally, the processing procedures, control procedures, specific names, and information including various kinds of data and parameters described herein or illustrated in the drawings can be optionally changed unless otherwise specifically noted.

Computer Program

It is also possible to create a computer program describing the processing performed by the information processing device described in the above embodiment in a computer-executable language. For example, it is possible to create a computer program describing the processing performed by the estimating device 10 according to the embodiment in a computer-executable language. In this case, the same effect as that of the embodiment described above can be obtained when the computer executes the computer program. Furthermore, such a computer program may be recorded in a computer-readable recording medium, and the computer program recorded in the recording medium may be read and executed by the computer to implement the same processing as that in the embodiment described above.

Figure 7:
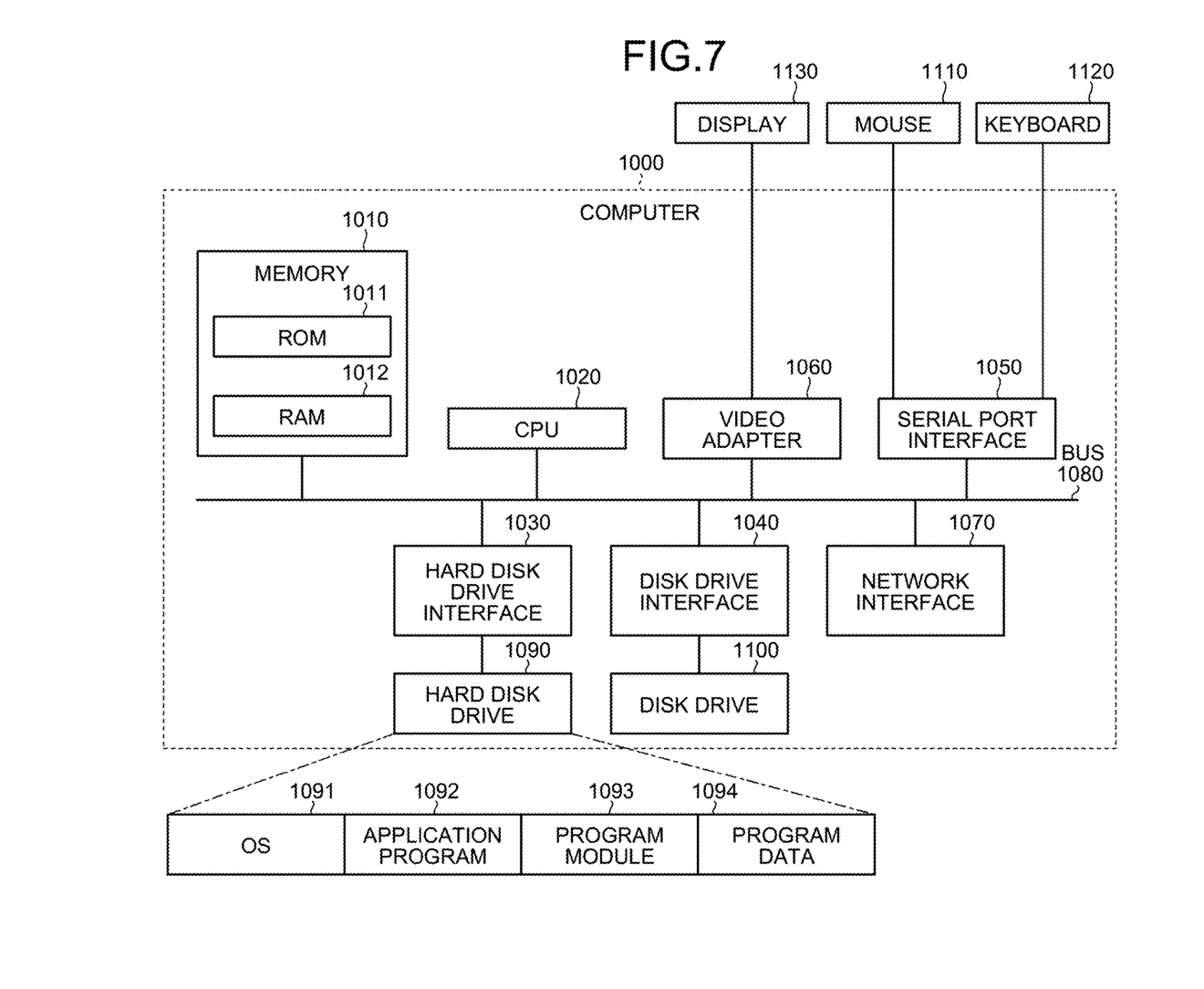
FIG. 7 is a diagram illustrating a computer that executes an estimating program.

FIG. 7 is a diagram illustrating the computer that executes the estimating program. As exemplified in FIG. 7, a computer 1000 includes, for example, a memory 1010, a CPU 1020, a hard disk drive interface 1030, a disk drive interface 1040, a serial port interface 1050, a video adapter 1060, and a network interface 1070, which are connected to each other via a bus 1080.

As exemplified in FIG. 7, the memory 1010 includes a read only memory (ROM) 1011 and a RAM 1012. The ROM 1011 stores, for example, a boot program such as a Basic Input Output System (BIOS). As exemplified in FIG. 7, the hard disk drive interface 1030 is connected to a hard disk drive 1090. As exemplified in FIG. 7, the disk drive interface 1040 is connected to a disk drive 1100. For example, a detachable storage medium such as a magnetic disc or an optical disc is inserted into the disk drive 1100. As exemplified in FIG. 7, the serial port interface 1050 is connected to a mouse 1110 and a keyboard 1120, for example. As exemplified in FIG. 7, the video adapter 1060 is connected to a display 1130, for example.

Herein, as exemplified in FIG. 7, the hard disk drive 1090 stores, for example, an OS 1091, an application program 1092, a program module 1093, and program data 1094. That is, the computer program described above is stored in the hard disk drive 1090, for example, as a program module describing a command executed by the computer 1000.

The various kinds of data described in the above embodiment are stored in the memory 1010 or the hard disk drive 1090, for example, as program data. The CPU 1020 then reads out the program module 1093 or the program data 1094 stored in the memory 1010 or the hard disk drive 1090 into the RAM 1012 as needed, and performs various processing procedures.

The program module 1093 and the program data 1094 related to the computer program are not necessarily stored in the hard disk drive 1090, but may be stored in a detachable storage medium, for example, and may be read out by the CPU 1020 via a disk drive and the like. Alternatively, the program module 1093 and the program data 1094 related to the computer program may be stored in another computer connected via a network (a local area network (LAN), a wide area network (WAN), and the like), and may be read out by the CPU 1020 via the network interface 1070.

According to the present invention, accuracy of authentication processing can be maintained even with image data including only part of a body of a person.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An estimating device comprising:
   processing circuitry configured to:
   acquire image data lacking part of a body of a person;
   restore a defective part of the body of the person in the image data by using the image data acquired as an input, and using a whole body restoration model for restoring the defective part of the body of the person in the image data; and
   estimate skeleton data by using the image data restored as an input, and using a skeleton estimation model for estimating the skeleton data related to a skeleton of the person.

2. The estimating device according to claim 1, wherein the processing circuitry is further configured to:
   compute a similarity between the skeleton data estimated and skeleton data registered in advance, and
   determine whether the similarity computed is equal to or larger than a predetermined threshold, determine that authentication has succeeded in a case in which the similarity is equal to or larger than the predetermined threshold, and determines that authentication has failed in a case in which the similarity is smaller than the predetermined threshold.

3. An estimating method comprising:
   acquiring image data lacking part of a body of a person;
   restoring a defective part of the body of the person in the image data by using the image data acquired at the acquiring as an input, and using a whole body restoration model for restoring the defective part of the body of the person in the image data; and
   estimating skeleton data by using the image data restored at the restoring as an input, and using a skeleton estimation model for estimating the skeleton data related to a skeleton of the person, by processing circuitry.

4. A non-transitory computer-readable recording medium storing therein an estimating program that causes a computer to execute a process comprising:
   acquiring image data lacking part of a body of a person;
   restoring a defective part of the body of the person in the image data by using the image data acquired at the acquiring as an input, and using a whole body restoration model for restoring the defective part of the body of the person in the image data; and
   estimating skeleton data by using the image data restored at the restoring as an input, and using a skeleton estimation model for estimating the skeleton data related to a skeleton of the person.

* * * * *